(12) United States Patent
Hallack et al.

(10) Patent No.: US 10,239,898 B2
(45) Date of Patent: Mar. 26, 2019

(54) COMPOUNDS BASED ON ADDUCTS WITH ISOCYANATES FOR COATING COMPOSITIONS

(71) Applicant: Evonik Degussa GmbH, Essen (DE)

(72) Inventors: Markus Hallack, Schermbeck (DE); Yvonne Schiemann, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/834,495

(22) Filed: Dec. 7, 2017

(65) Prior Publication Data

US 2018/0179234 A1    Jun. 28, 2018

(30) Foreign Application Priority Data

Dec. 22, 2016 (EP) ..................... 16206306

(51) Int. Cl.
| | | |
|---|---|---|
| *C09D 175/04* | (2006.01) | |
| *C07F 7/18* | (2006.01) | |
| *C09D 183/08* | (2006.01) | |
| *C09D 5/16* | (2006.01) | |
| *C08K 5/21* | (2006.01) | |

(52) U.S. Cl.
CPC .......... *C07F 7/1804* (2013.01); *C09D 5/1625* (2013.01); *C09D 175/04* (2013.01); *C09D 183/08* (2013.01); *C08K 5/21* (2013.01)

(58) Field of Classification Search
CPC ............................. C07F 7/1836; C09D 5/1625
See application file for complete search history.

(56) References Cited

U.S. PATENT DOCUMENTS

| | | | |
|---|---|---|---|
| 6,441,213 | B1 | 8/2002 | Musa et al. |
| 6,794,445 | B2 | 9/2004 | Hallack et al. |
| 9,266,825 | B2 | 2/2016 | Lomoelder |
| 9,655,934 | B2 | 5/2017 | Schiemann et al. |
| 9,765,366 | B2 | 9/2017 | Schiemann et al. |
| 9,796,876 | B2 | 10/2017 | Lomoelder et al. |
| 9,902,095 | B2 | 2/2018 | Stapperfenne et al. |
| 9,902,096 | B2 | 2/2018 | Stapperfenne et al. |
| 2004/0161438 | A1 | 8/2004 | Schiemann et al. |
| 2007/0028825 | A1 | 2/2007 | Martensson |
| 2007/0203307 | A1 | 8/2007 | Schiemann et al. |
| 2011/0052522 | A1 | 3/2011 | Schiemann et al. |
| 2015/0267231 | A1 | 9/2015 | Hass et al. |
| 2016/0017165 | A1 | 1/2016 | Numrich et al. |
| 2016/0108280 | A1 | 4/2016 | Hallack et al. |
| 2016/0138058 | A1 | 5/2016 | Wittmann et al. |
| 2016/0297974 | A1 | 10/2016 | Stache et al. |
| 2017/0298250 | A1 | 10/2017 | Anselmann et al. |

FOREIGN PATENT DOCUMENTS

| | | |
|---|---|---|
| DE | 102009014685 A1 | 9/2010 |
| WO | 2009135739 | 11/2009 |
| WO | 2013000717 | 1/2013 |
| WO | 2013186340 | 12/2013 |
| WO | 2013189882 | 12/2013 |
| WO | 2014135353 | 9/2014 |
| WO | 2014139752 | 9/2014 |
| WO | 2014180623 | 11/2014 |
| WO | 2014198560 | 12/2014 |
| WO | 2015011177 A1 | 1/2015 |
| WO | 2016037843 | 3/2016 |
| WO | 2017055418 | 4/2017 |

OTHER PUBLICATIONS

Kumagaya et al (2000): STN International, HCAPLUS database (Columbus, Ohio), Accession No. 2000: 748833.*
European Search Report dated Jul. 7, 2017 in EP 16206306.9 (6 pages).
Vasar et al., "Synthesis and Properties of Imidazole-Blocked Toluene Diisocyanates," copyright 1997, Journal of Macromolecular Science, Part A—Pure and Applied Chemistry, Marcel Dekker, Inc., US, pp. 1237-1247 (11 pages).

* cited by examiner

*Primary Examiner* — Golam M Shameem
(74) *Attorney, Agent, or Firm* — Philip P. McCann; Nexsen Pruet, PLLC

(57) ABSTRACT

The present invention relates to compounds based on adducts with isocyanates. The present invention further relates to a method for preparation thereof, compositions comprising these compounds and also use thereof as, or for producing, coatings.

3 Claims, 6 Drawing Sheets

```
Current Data Parameters
NAME         sta01816
EXPNO              20
PROCNO              1

F2 - Acquisition Parameters
Date_        20150204
Time            23.18
INSTRUM          spect
PROBHD   5 mm CPPBBO BB
PULPROG         zgig30
TD               65536
SOLVENT  CDCl3+Cr(acac)3
NS                1024
DS                   4
SWH        37593.984 Hz
FIDRES      0.573639 Hz
AQ         0.8716288 sec
RG                2048
DW            13.300 usec
DE             6.00 usec
TE             303.0 K
D1        3.00000000 sec
D11       0.03000000 sec
TDO                  1

======== CHANNEL f1 ========
NUC1                13C
P1              9.90 usec
PL1              0.60 dB
PL1W       79.85330200 W
SFO1     125.7559045 MHz ======== CHANNEL f2 ========
CPDPRG[2       waltz16
NUC2                1H
PCPD2          80.00 usec
PL2             -4.50 dB
PL12            15.12 dB
PL2W       21.23837280 W
PL12W       0.23180418 W
SFO2     500.0630000 MHz F2 - Processing parameters
SI               65536
SF       125.7401628 MHz
WDW                 EM
SSB                  0
LB              1.00 Hz
GB                   0
PC                1.40
```

Figure 1 b

```
Current Data Parameters
NAME        sta01816
EXPNO            21
PROCNO            1

F2 - Acquisition Parameters
Date_       20150204
Time           23.26
INSTRUM         spect
PROBHD   5 mm CPPBBO BB
PULPROG       dept135
TD            65536
SOLVENT  CDCl3+Cr(acac)3
NS              128
DS                4
SWH       32679.738 Hz
FIDRES     0.498653 Hz
AQ         1.0027008 sec
RG           2580.3
DW           15.300 usec
DE            6.00 usec
TE            303.0 K
CNST2     145.0000000
D1         2.00000000 sec
D2         0.00344828 sec
D12        0.00002000 sec
TD0               1

======== CHANNEL f1 ========
NUC1             13C
P1            9.90 usec
P2           19.80 usec
PL1           0.60 dB
PL1W      79.85330200 W
SFO1      125.7527610 MHz ======== CHANNEL f2 ========
CPDPRG[2      waltz16
NUC2             1H
P3            9.40 usec
P4           18.80 usec
PCPD2        80.00 usec
PL2          -4.50 dB
PL12         15.12 dB
PL2W      21.23837280 W
PL12W      0.23180418 W
SFO2      500.0620000 MHz F2 - Processing parameters
SI            32768
SF        125.7401626 MHz
WDW              EM
SSB               0
LB            1.00 Hz
GB                0
PC             1.40
```

Figure 2 b

COMPOUNDS BASED ON ADDUCTS WITH ISOCYANATES FOR COATING COMPOSITIONS

This application claims the benefit of European Application No. 16206306.9 filed on Dec. 22, 2016, the disclosure of which is expressly incorporated herein by reference.

FIELD

The present invention relates to compounds based on adducts with isocyanates. The present invention further relates to a method for preparation thereof, compositions comprising these compounds and also use thereof as, or for producing, coatings.

BACKGROUND

Ship coatings are used as topcoat on ships' hulls or other underwater structures in order to prevent the colonization and growth of marine organisms, such as barnacles or algae for example, so-called biofouling. In the context of the present invention, underwater structures refer to the bottom or hulls of ships, constituents on and below the waterline of watercraft, solid banks, nets, port facilities, wind turbines, buoys, pipelines, bridges, aquaculture nets, facilities related to submarines, offshore installations such as drilling platforms, pipes, wavebreakers or marine anchors.

This growth or biofouling has historically been a considerable disruptive factor for the marine industry and shipping. The organic growth consists especially of barnacles, mussels, fungi, snails, algae and further microorganisms in which algae are the carrier material for macrofouling.

Like all objects present in seawater, a hull or a ship's propeller can be fouled completely within a few months with so-called biofoulers. The water resistance of a completely fouled hull increases immensely in this case and with it an increase of fuel costs of up to 40%, which result in marked economic and ecological influences. In addition, the controllability may be impaired, which represents an enormous safety risk and also leads to damage to the ship's hull.

To maintain the antifouling of maritime ships today places a series of various requirements on ship coatings. They should on the one hand be cost-effective while on the other hand have the longest possible service life. Additionally, they are dependent on a high and continuous efficacy as far as possible against all potential fouling organisms, a low surface roughness, a high resistance to mechanical and chemical stresses and favourable docking intervals.

The docking intervals of maritime ships are not however defined by fouling of ships' hulls but are determined by the classification societies or by the provisions of ship regulations. The average docking interval of the world's merchant fleet is currently just under 30 months. According to the specification of the classification societies, standard ships are to be taken into dock after an operating period of 2.5 years so that the ship's bottom can be investigated in the context of an intermediate inspection. After a further 2.5 years' operation, the renewal of the class is pending which in turn makes docking unavoidable. Moreover, all passenger ships have to meet ongoing regulations. They have to be annually inspected in the dock. An increasing number of ships are equipped such that the intermediate inspection may also be conducted in floating condition (In Water Survey, IWS). By means of an IWS, one docking per class period (5 years) is eliminated. Since an IWS ship therefore remains in the water for 60 months, this has to be taken into account when choosing the corrosion protection and the antifouling system.

The use of organotin compounds has been forbidden in the EU since 2003, and therefore the most widely used paint up to that point based on tributyl tin (TBT) may no longer be used. In addition, all old stocks of TBT on ships' hulls had to be removed by 2008. TBT had fallen into disrepute, especially owing to its hormone-like property, which had created in whelks, inter alia, in the North Sea for example, a high proportion of sterile individuals. In principle, it is apparent that chemically effective protective paints which are based on the controlled release of biocidal substances such as TBT, copper or organic active ingredients, are increasingly being replaced by novel research approaches. Since the risk of long-term consequences or harm of chemical fouling protection methods in the past could only be assessed with difficulty, nowadays effort is being made to develop ecologically compatible antifouling techniques, so-called "non-toxic" antifoulings.

Due to the EU biocide guideline of 1998, all active ingredients used to date and likewise all new active ingredients appearing must be tested. The aim is to forbid all chemicals which are carcinogenic, which alter genetic material, which impair fertility and also are persistent and accumulate in food chains. Only when there is no alternative are certain biocides approved for a transitional period. Following a positive evaluation, these are then included in Appendix I/IA of the guideline of the EU and may be used. In the case of a negative assessment, the active ingredients are published in a list of non-approved active ingredients and must be taken off the market within 12 months. There are currently ca. 35 substances on the list of active ingredients no longer approved for antifouling, among them formaldehyde, Captan CAS Reg. No. [133-06-2] and the formerly very frequently used Diuron CAS Reg. No. [330-54-1]. The evaluation of other existing substances is currently being conducted.

DE102009014685 A1 describes the use of solvent-free and light-resistant coating materials based on an amino- and/or hydroxyl-group functional reaction partner, which can be crosslinked with isocyanates, which exhibit an antimicrobial effect based on metal ions, especially silver cations.

SUMMARY

The object of the invention consisted of providing novel compounds for ship coatings, the use of which counteracts the effects mentioned, such as the colonization of ship's hulls or other underwater structures by marine organisms. Furthermore, an object of the present invention consisted of developing a compliant and effective agent in accordance with the legal biocide criteria, for example the EU biocide guideline of 1998. In particular, it is an object of the present invention to provide compounds for coating compositions which do not contain any of the substances that are legally no longer approved, such as trialkyltin derivatives.

BRIEF DESCRIPTION OF THE DRAWINGS

FIG. 1a representatively shows a $^{13}$C-NMR spectrum of a specific chemical sample;

FIG. 1b representatively shows a printout of information for the $^{13}$C-NMR spectrum of FIG. 1a;

FIG. 2a representatively shows a $^{13}$C-NMR spectrum of a specific chemical sample;

FIG. 2b representatively shows a printout of information for the $^{13}$C-NMR spectrum of FIG. 2a;

DETAILED DESCRIPTION

Figure 1:
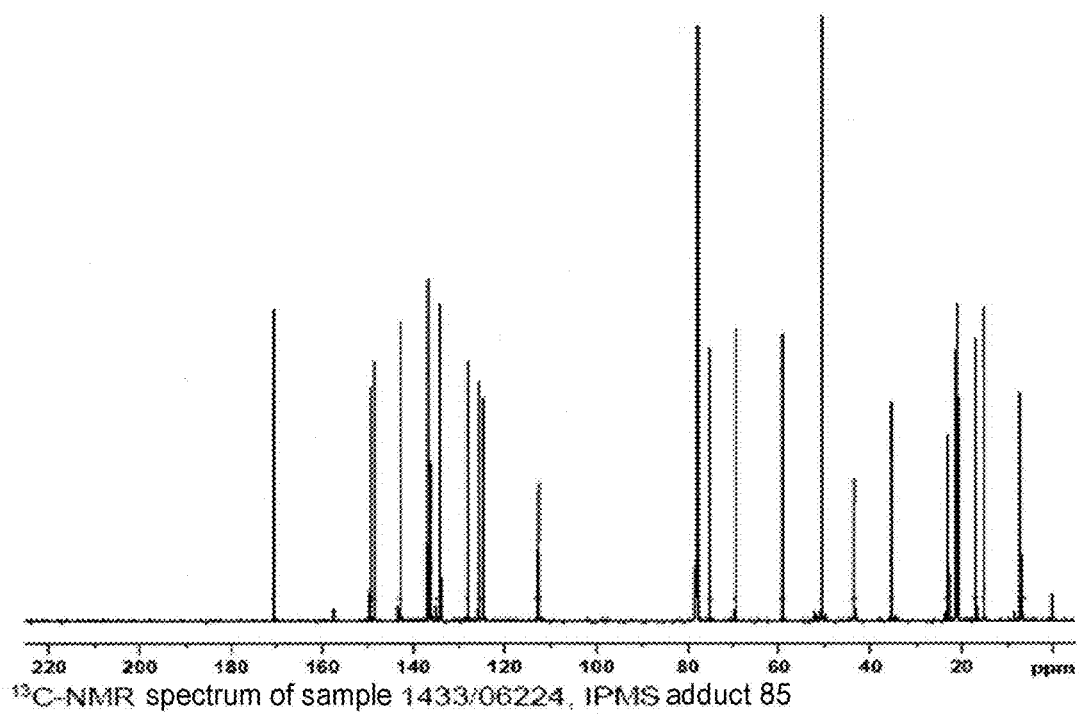

This object is achieved by a compound of the formula (1):

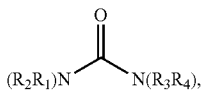
(1)

characterized in that $R_1$=selected from the group of substituted or unsubstituted aliphatic radicals, substituted or unsubstituted aromatic radicals, substituted or unsubstituted cycloaliphatic radicals, substituted or unsubstituted heterocyclic radicals or alkoxy-substituted silylalkyl radicals, preferably alkoxy-substituted silylalkyl radicals, $R_2$=H and $R_3$ and $R_4$, identical or different, are selected from the group of substituted or unsubstituted aliphatic radicals, substituted or unsubstituted aromatic radicals, substituted or unsubstituted cycloaliphatic radicals, substituted or unsubstituted heterocyclic radicals or hydrogen, wherein the radicals $R_3$ and $R_4$ may be bonded to each other and may form a heterocyclic structure.

The present invention further relates to a method for preparing the compound (1) according to the invention.

The present invention also relates to the use of the compound (1) according to the invention in compositions for coating underwater structures to protect against colonization and/or growth of marine organisms.

The present invention further relates to a method for applying the composition according to the invention, in which the reaction to give a compound (1) according to the invention takes place by bringing into contact at least one isocyanate group-containing compound, as defined below, and at least one pharmacologically active compound comprising at least one amine group, as defined below, by applying them to the substrate to be coated. The substrate to be coated is understood to mean preferably the underwater structures mentioned at the outset.

By way of preference, the compound (1) according to the invention is characterized in that $R_3$ and $R_4$ are bonded to each other and preferably form a heterocyclic structure, particularly preferably a heteroaromatic structure.

It is advantageous in the context of the present invention if the heteroaromatic structure of the compound described herein comprises an unsubstituted or substituted imidazole ring. It is particularly advantageous if the compound described herein has a structure of the formula (2):

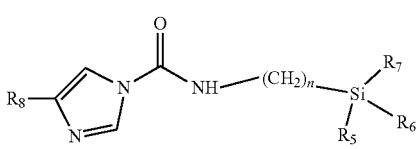
(2)

where n=1-8, $R_5$, $R_6$, $R_7$ are each independently selected from the group of C1-C3-alkoxy radicals, $R_8$ is selected from the group of alkyl, aralkyl or heteroaralkyl radicals.

The compound according to the invention particularly preferably has the structure of the following formula (3):

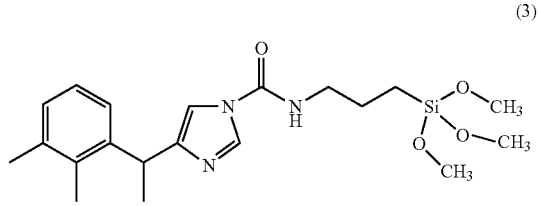
(3)

The present invention further relates to compositions comprising the compound (1) according to the invention.

The composition according to the invention is preferably characterized in that said composition comprises the compound of the formula (3). It is advantageous in the context of the present invention if the composition described herein comprises an adhesion promoter, preferably selected from the group comprising aminosilanes, aminoalkylsilanes or alkoxysilylalkyl-substituted amines of the formula (6):

$A_mSiY_n$ (6),

A is a substituted or unsubstituted aminoalkyl group, a substituted or unsubstituted diaminodialkyl group or substituted or unsubstituted triaminotrialkyl group, the groups Y are identical or different, and Y is OH, ONa, OK, OR', OCOR', OSiR'$_3$, Cl, Br, I or NR'$_2$, m is 1 or 2 and n is 1, 2 or 3, with the proviso that m+n=4, and the group R' independently is hydrogen, linear or branched alkyl, cycloalkyl, alkenyl, cycloalkenyl, alkynyl, cycloalkynyl, aryl or heteroaryl groups, have in each case 1 to 18 carbon atoms and may in each case optionally be substituted.

It is preferable when m is 1 and n is 3. It is further preferable when Y is selected from OH or OR', particular preference being given to OR'. In this case R' is in particular selected from methyl or ethyl groups, particular preference being given to methyl groups.

Such aminosilanes, aminoalkylsilanes or alkoxysilylalkyl-substituted amines are, for example but not exclusively, 3-aminopropyltrimethoxysilane, 3-aminopropyltriethoxysilane, 2-aminoethyl-3-aminopropyltrimethoxysilane, 3-aminopropyl(diethoxymethoxysilane), 3-aminopropyl(tripropoxysilane), 3-aminopropyl(dipropoxymethoxysilane), 3-aminopropyl(tridodecanoxysilane), 3-aminopropyl(tritetradecanoxysilane), 3-aminopropyl(trihexadecanoxysilane), 3-aminopropyl(trioctadecanoxysilane), 3-aminopropyl(didodecanoxy)tetradecanoxysilane, 3-aminopropyl(dodecanoxy)tetradecanoxy(hexadecanoxy) silane, 3-aminopropyl(dimethoxymethylsilane), 3-aminopropyl(methoxydimethylsilane), 3-aminopropyl(hydroxydimethylsilane), 3-aminopropyl(diethoxymethylsilane), 3-aminopropyl(ethoxydimethylsilane), 3-aminopropyl(dipropoxymethylsilane), 3-aminopropyl(propoxydimethylsilane), 3-aminopropyl(diisopropoxymethylsilane), 3-aminopropyl(isopropoxydimethylsilane), 3-aminopropyl(dibutoxymethylsilane), 3-aminopropyl(butoxydimethylsilane), 3-aminopropyl(diisobutoxymethylsilane), 3-aminopropyl(isobutoxydimethylsilane), 3-aminopropyl(didodecanoxymethylsilane), 3-aminopropyl(dodecanoxydimethylsilane), 3-aminopropyl(ditetradecanoxymethylsilane), 3-aminopropyl(tetradecanoxydimethylsilane), 2-aminoethyl (trimethoxysilane), 2-aminoethyl(triethoxysilane), 2-aminoethyl(diethoxymethoxysilane), 2-aminoethyl(tripropoxysilane), 2-aminoethyl(dipropoxymethoxysilane), 2-aminoethyl(tridodecanoxysilane), 2-aminoethyl(tritetradecanoxysilane), 2-aminoethyl(trihexadecanoxysilane), 2-aminoethyl(trioctadecanoxysilane), 2-aminoethyl(didodecanoxy)tetradecanoxysilane, 2-aminoethyl(dodecanoxy)tetradecanoxy(hexadecanoxy)silane, 2-aminoethyl(dimethoxymethylsilane), 2-aminoethyl(methoxydimethylsilane), 2-aminoethyl(diethoxymethylsilane), 2-aminoethyl(ethoxydimethylsilane), 1-aminomethyl(trimethoxysilane), 1-aminomethyl(triethoxysilane), 1-aminomethyl(diethoxymethoxysilane), 1-aminomethyl(dipropoxymethoxysilane), 1-aminomethyl(tripropoxysilane), 1-aminomethyl (trimethoxysilane), 1-aminomethyl(dimethoxymethylsilane), 1-aminomethyl(methoxydimethylsilane), 1-aminomethyl(diethoxymethylsilane), 1-aminomethyl (ethoxydimethylsilane), 3-aminobutyl(trimethoxysilane), 3-aminobutyl(triethoxysilane), 3-aminobutyl(diethoxymethoxysilane, 3-aminobutyl(tripropoxysilane), 3-aminobutyl(dipropoxymethoxysilane), 3-aminobutyl(dimethoxymethylsilane), 3-aminobutyl(diethoxymethylsilane), 3-aminobutyl(dimethylmethoxysilane), 3-aminobutyl (dimethylethoxysilane), 3-aminobutyl(tridodecanoxysilane), 3-aminobutyl(tritetradecanoxysilane), 3-aminobutyl(trihexadecanoxysilane), 3-aminobutyl(didodecanoxy)tetradecanoxysilane, 3-aminobutyl(dodecanoxy)tetradecanoxy(hexadecanoxy)silane, 3-amino-2-methylpropyl (trimethoxysilane), 3-amino-2-methylpropyl(triethoxysilane), 3-amino-2-methylpropyl(diethoxymethoxysilane), 3-amino-2-methylpropyl(tripropoxysilane), 3-amino-2-methylpropyl(dipropoxymethoxysilane), 3-amino-2-methylpropyl(tridodecanoxysilane), 3-amino-2-methylpropyl(tritetradecanoxysilane), 3-amino-2-methylpropyl(trihexadecanoxysilane), 3-amino-2-methylpropyl(trioctadecanoxysilane), 3-amino-2-methylpropyl(didodecanoxy)tetradecanoxysilane, 3-amino-2-methylpropyl(dodecanoxy) tetradecanoxy(hexadecanoxy)silane, 3-amino-2-methylpropyl(dimethoxymethylsilane), 3-amino-2-methylpropyl (methoxydimethylsilane), 3-mercapto-2-methylpropyl(diethoxymethylsilane), 3-mercapto-2-methylpropyl(ethoxydimethylsilane), 3-mercapto-2-methylpropyl(dipropoxymethylsilane), 3-amino-2-methylpropyl(propoxydimethylsilane), 3-amino-2-methylpropyl(diisopropoxymethylsilane), 3-amino-2-methylpropyl(isopropoxydimethylsilane), 3-amino-2-methylpropyl(dibutoxymethylsilane), 3-amino-2-methylpropyl(butoxydimethylsilane), 3-amino-2-methylpropyl(diisobutoxymethylsilane), 3-amino-2-methylpropyl (isobutoxydimethylsilane), 3-amino-2-methylpropyl(didodecanoxymethylsilane), 3-amino-2-methylpropyl(dodecanoxydimethylsilane), 3-amino-2-methylpropyl(ditetradecanoxymethylsilane) or 3-amino-2-methylpropyl (tetradecanoxydimethylsilane), triamino-functional propyltrimethoxysilane, bis(3-trimethoxysilylpropyl)amine, bis(3-triethoxysilylpropyl)amine, N-benzyl-N-(2-aminoethyl)-3-aminopropyltrimethoxysilane hydrochloride, N-benzyl-N-(2-aminoethyl)-3-aminopropyltrimethoxysilane hydroacetate, N-(n-butyl)-3-aminopropyltrimethoxysilane, 3-aminopropylmethyldiethoxysilane, N-vinylbenzyl-N-(2-aminoethyl)-3-aminopropylpolysiloxane and N-(2-aminoethyl)-3-aminopropylmethyldimethoxysilane.

Preferred aminosilanes, aminoalkylsilanes or alkoxysilylalkyl-substituted amines are substituted or unsubstituted aminosilane compounds, in particular 3-aminopropyltrimethoxysilane, 3-aminopropyltriethoxysilane, 3-aminopropylmethyldiethoxysilane, N-(2-aminoethyl)-3-aminopropyltrimethoxysilane, 2-aminopropyl-3-aminopropyltrimethoxysilane, 2-aminopropyl-3-aminopropyltriethoxysilane, 2-aminoethyl-2-aminoethyl-3-aminopropyltrimethoxysilane, 2-aminoethyl-2-aminoethyl-3-aminopropyltriethoxysilane and N-(n-butyl)-3-aminopropyltrimethoxysilane. As aminosilanes of the formula (6), particular preference is given to using 3-aminopropyltrimethoxysilane (DYNASYLAN® AMMO), 3-aminopropyltriethoxysilane (DYNASYLAN® AMEO), 3-aminopropylmethyldiethoxysilane (DYNASYLAN® 1505), N-(n-butyl)-3-aminopropyltrimethoxysilane (DYNASYLAN® 1189) and N-(2-aminoethyl)-3-aminopropyltrimethoxysilane (DYNASYLAN® DAMO), $(H_3CO)_3Si(CH_2)_3NH(CH_2)_3Si(OCH_3)_3$ (bis-AMMO), $(H_5C_2O)_3Si(CH_2)_3NH(CH_2)_3Si(OC_2H_5)_3$ (bis-AMEO), $(H_3CO)_3Si(CH_2)_3NH(CH_2)_2NH(CH_2)_2NH(CH_2)_3Si(OCH_3)_3$ (bis-DAMO), each from Evonik Industries AG.

The present invention also addresses a method for preparing the compound (1) according to the invention comprising the following steps:
a) providing at least one isocyanate group-containing compound of the formula R—N=C=O (4), where R is selected from the group comprising substituted or unsubstituted aliphatic, aromatic, cycloaliphatic, heterocyclic radicals and alkoxysilylalkyl radicals, preferably alkoxysilylalkyl radicals,
b) providing at least one compound from the group of pharmacologically active compounds comprising at least one amine group;
c) reacting the compounds specified in steps a) and b) in the presence of a catalyst.

The at least one isocyanate group-containing compound provided in step a) preferably has a structure of the following formula (5):

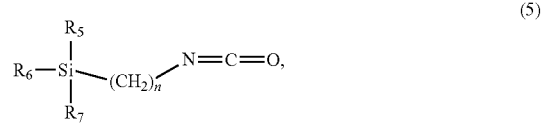

where n=1-8 and $R_5$, $R_6$, $R_7$ are each independently selected from the group of C1-C3-alkoxy radicals.

Examples of suitable compounds of the formula (5) are isocyanatoalkylalkoxysilanes, selected more particularly from the group comprising 3-isocyanatopropyltrimethoxysilane, 3-isocyanatopropyltriethoxysilane, 3-isocyanatopropyltriisopropoxysilane, 2-isocyanatoethyltrimethoxysilane, 2-isocyanatoethyltriethoxysilane, 2-isocyanatoethyltriisopropoxysilane, 4-isocyanatobutyltrimethoxysilane, 4-isocyanatobutyltriethoxysilane, 4-isocyanatobutyltriisopropoxysilanes, isocyanatomethyltrimethoxysilane, isocyanatomethyltriethoxysilane and/or isocyanatomethyltriisopropoxysilane.

Particularly preferred for use as compound of the formula (5) are 3-isocyanatopropyltrialkoxysilanes, more particularly 3-isocyanatopropyltrimethoxysilane and/or 3-isocyanatopropyltriethoxysilane.

In the context of the present invention, the pharmacologically active compounds include, for example, biocide products for human hygiene, disinfectants for the private sector and the public health sector and other biocide products, biocide products for hygiene in the veterinary sector, disinfectants for the food and feed industry, drinking water disinfectants, in-can preservatives, coating protectants, wood protectants, protectants for fibres, leather, rubber and polymerized materials, protectants for brickwork, preservatives for liquids in cooling and processing systems, slimicides, protectants for metal processing liquids, rodenticides, avicides, molluscicides, piscicides, insecticides, acaricides and products against other arthropods, repellants and attractants, preservatives for food and feed, antifouling products, liquids for embalming and taxidermy, products against other vertebrates.

The pharmacologically active compounds, comprising at least one amine group, provided in step b) preferably have a heterocyclic structure, particularly a heteroaromatic structure.

By way of preference, the pharmacologically active compounds comprising at least one amine group, provided in the method described herein in step b), have an imidazole structure, in particular an imidazole structure substituted by an aralkyl radical.

The pharmacologically active compounds provided in step b) are particularly preferably selected from compounds having the CAS registry numbers 86347-14-0, 86347-15-1, 113775-47-6 and/or 106807-72-1.

In the method according to the invention, the reaction in step c) is preferably carried out under catalysis. Suitable for catalysis of the method described herein are, for example, tin-containing compounds, preference being given to dialkyltin carboxylates for example. Particular preference is given to, e.g. di-n-butyltin diacetate, di-n-butyltin dilaurate, di-n-butyltin maleate, di-n-butyltin bis-2-ethylhexanoate and di-n-butyltin dineodecanoate, dioctyltin carboxylates such as di-n-octyltin diacetate, di-n-octyltin dilaurate, di-n-octyltin maleate, di-n-octyltin bis-2-ethylhexanoate or di-n-octyltin dineodecanoate. The amount of tin-containing compound used for the catalysis is 0.001 to 0.1% by weight, preferably 0.001 to 0.01% by weight, based on the reactants used in step a) and step b).

In step c), the at least one isocyanate group-containing compound (4) and the pharmacologically active compound are preferably reacted in equimolar amounts. The reaction is carried out advantageously down to a residual isocyanate content of less than 0.1% by weight, based on the reactants used in step a) and step b). The isocyanate content is determined in accordance with DIN EN ISO 11909.

The reaction can be preferably conducted in the absence of solvent or using aprotic solvents and the reaction may be carried out in batchwise mode or continuously. The reaction can be carried out at room temperature, in other words at temperatures in the range of 20-25° C., although preference is given to using higher temperatures in the range of 30-150° C., more particularly in the range of 50-150° C. Aprotic solvents are understood to mean those solvents with molecules having a low polarity, for example due to the absence of hydroxyl groups. Suitable aprotic solvents include the group of alkylene glycol ether carboxylates such as methoxypropyl acetates for example. It is advantageous to carry out the reaction with stirring.

In a preferred embodiment of the method according to the invention, the compound (1) according to the invention, or one of its embodiments or the reaction product of the method for the preparation thereof described hereinabove, is obtained in a composition. For this purpose, the compound (1) according to the invention or one of its embodiments or the reaction product of the method for the preparation thereof described hereinabove is further mixed with an adhesion promoter of the formula (6), as described above.

In the method for preparing a composition, the compound (1) according to the invention or one of its embodiments or the reaction product of the method for the preparation thereof described hereinabove is preferably mixed under catalysis with an adhesion promoter of the formula (6) described above.

Preferred adhesion promoters are selected from 3-aminopropyltrimethoxysilane, 3-aminopropyltriethoxysilane, 3-aminopropylmethyldiethoxysilane, N-(2-aminoethyl)-3-aminopropyltrimethoxysilane, 2-aminopropyl-3-aminopropyltrimethoxysilane, 2-aminopropyl-3-aminopropyltriethoxysilane, 2-aminoethyl-2-aminoethyl-3-aminopropyltrimethoxysilane, 2-aminoethyl-2-aminoethyl-3-aminopropyltriethoxysilane and N-(n-butyl)-3-aminopropyltrimethoxysilane. As aminosilanes of the formula (6), particular preference is given to using 3-aminopropyltrimethoxysilane (DYNASYLAN® AMMO), 3-aminopropyltriethoxysilane (DYNASYLAN® AMEO), 3-aminopropylmethyldiethoxysilane (DYNASYLAN® 1505), N-(n-butyl)-3-aminopropyltrimethoxysilane (DYNASYLAN® 1189) and N-(2-aminoethyl)-3-aminopropyltrimethoxysilane (DYNASYLAN® DAMO), $(H_3CO)_3Si(CH_2)_3NH(CH_2)_3Si(OCH_3)_3$ (bis-AMMO), $(H_5C_2O)_3Si(CH_2)_3NH(CH_2)_3Si(OC_2H_5)_3$ (bis-AMEO), $(H_3CO)_3Si(CH_2)_3NH(CH_2)_2NH(CH_2)_2NH(CH_2)_3Si(OCH_3)_3$ (bis-DAMO), each from Evonik Industries AG.

Suitable for catalysis of this embodiment of the method according to the invention are, for example, tin-containing compounds, preference being given to dialkyltin carboxylates for example. Particular preference is given to, e.g. di-n-butyltin diacetate, di-n-butyltin dilaurate, di-n-butyltin maleate, di-n-butyltin bis-2-ethylhexanoate and di-n-butyltin dineodecanoate, dioctyltin carboxylates such as di-n-octyltin diacetate, di-n-octyltin dilaurate, di-n-octyltin maleate, di-n-octyltin bis-2-ethylhexanoate or di-n-octyltin dineodecanoate.

The amount of tin-containing compound used for the catalysis is 0.001 to 0.5% by weight, preferably 0.01 to 0.1% by weight, based on the amount of compound (1) according to the invention or one of its embodiments or the reaction product of the method for the preparation thereof described hereinabove and the adhesion promoter of the formula (6) used, as described above.

The present invention further relates to a method for applying the composition according to the invention, in which the reaction to give a compound (1) according to the invention takes place by bringing into contact at least one isocyanate group-containing compound of the formula R—N=C=O (4), and at least one pharmacologically active compound comprising at least one amine group, as defined above, by applying them to the substrate to be coated.

The present invention further relates to the use of the compound (1) according to the invention, or one of its embodiments or the reaction product of the method for the preparation thereof described hereinabove, as or for the production of coatings, particularly coatings of underwater structures, preferably for protection against colonization and/or growth of marine organisms.

In one embodiment of this use, the composition according to the invention is applied to the underwater structures, wherein the curing and formation of a coating preferably takes place at room temperature, i.e. at temperatures in the range of 20-25° C.

The pharmacologically active compounds covered by the aforementioned CAS registry numbers 86347-14-0, 86347-15-1, 113775-47-6 and/or 106807-72-1, in addition to the systematic name for the racemate (RS)-4-[1-(2,3-dimethylphenyl)ethyl]-1H-imidazole, are disclosed under the general name medetomidine. Medetomidine is known for its use in veterinary and human medicine as a sedative and analgesic.

US 2007/0028825 A1 and WO 2015011177 A1 disclose the use of medetomidine, as described above, physically dissolved or in suspended form in a coating composition, in a paint for example, and sometimes also in mixtures with further substances active against marine organisms, in order to counteract growth or biofouling.

The inventors have now established, surprisingly, that the activity of medetomidine against growth or biofouling is preserved on underwater structures even when medetomidine, as described above, is converted in a chemical reaction with at least one isocyanate group-containing compound of the formula R—N═C═O (4) with formation of a covalent bond to give at least one adduct compound of the formula (1).

The reactivity of the reaction between medetomidine, as described above, and the at least one isocyanate group-containing compound of the formula R—N═C═O (4) to give a corresponding adduct compound of the formula (1) is sufficiently great that even 2-component systems for coating of underwater structures can be achieved, as has already been disclosed in some embodiments of the present invention.

The obvious advantage over the prior art, as disclosed for example in US 2007/0028825 A1 or WO 2015011177 A1, is in the chemical bonding of the pharmacologically active compound comprising at least one amine group, in particular medetomidine, as disclosed here, to at least one isocyanate group-containing compound. More surprising is also the fact that the activity of the compounds according to the invention against growth or biofouling of underwater structures is even preserved in a composition, for coating for example.

Leaching or significant depletion of the concentration of medetomidine in a composition according to the prior art, if it is not covalently bound as, for example, in an adduct compound with an isocyanate group-containing compound, is avoided by the teaching according to the invention. The protection of underwater structures from growth of marine organisms or biofouling is thereby prolonged in terms of time.

It is self-evident and intended that all embodiments which are disclosed herein in connection with the compounds and compositions described are applicable to the same extent to the uses and methods described and vice versa. Such embodiments therefore likewise fall within the scope of the present invention.

Without having any restricting effect themselves, the examples which follow are intended to elucidate in more detail the subject matter of the present invention.

Inventive Example 1: Preparation of Compound 3

101.60 g of 3-isocyanatopropyltrimethoxysilane, commercially available as Vestanat® EP-IPMS, are reacted in an equimolar amount with 98.38 g of medetomidine, commercially available as Selektope®. For the catalysis, 0.01% by weight of dibutyl dilauryl stannate is added. This mixture is heated to 60° C. with stirring over a period of 3 hours and, after a further 30 minutes, 20% by weight propylene glycol monomethyl ether acetate, commercially available as Dowanol™ PMA, is added as solvent. The solution is further stirred until a residual isocyanate content of <0.1% by weight—determined in accordance with DIN EN ISO 11909—is achieved; duration ca. 5 h. All percentage figures refer to the weights of the reactants 3-isocyanatopropyltrimethoxysilane and medetomidine. Subsequently, this solution is cooled to room temperature while stirring and the solvent is removed.

The $^{13}$C-NMR analytical investigation confirms the structure of compound 3 according to the invention disclosed above.

3-Isocyanatopropyltrimethoxysilane was fully converted to the adduct, the compound of the formula (3) according to the invention and accordingly the signal of the free NCO group at ca. 122 ppm has disappeared and a new carbonyl signal has appeared at 149 ppm.

The sample additionally comprises residues of the solvent methoxypropylene glycol acetate.

All signals are assigned in Table 1 which follows.

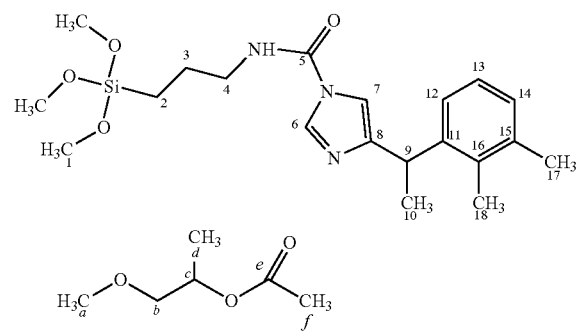

Compound (3)

Methoxypropylene glycol acetate

TABLE 1

| signal assignment $^{13}$C-NMR: | | | |
|---|---|---|---|
| Signal position [ppm] | Intensity | Multiplicity | Assignment |
| 170.6 | 0.7 | Cq | e |
| 149.4 | 1 | Cq | 5 |
| 148.4 | 1 | Cq | 8 |
| 142.7 | 1 | Cq | 11 |
| 136.7 | 1 | Cq | 16 |
| 136.0 | 1 | CH* | 6 |
| 134.0 | 1 | Cq | 15 |
| 128.0 | 1 | CH | 10 |
| 125.5 | 1 | CH | 13 |
| 124.5 | 1 | CH | 12 |
| 112.4 | 1 | CH* | 7 |
| 77.8 | — | Cq | CDCl$_3$ |
| 75.1 | 0.7 | CH$_2$ | b |
| 69.4 | 0.7 | CH | c |
| 59.0 | 0.7 | CH$_3$ | a |
| 50.5 | 3 | CH$_3$ | 1 |
| 43.2 | 1 | CH$_2$ | 4 |
| 35.3 | 1 | CH | 9 |
| 22.7 | 1 | CH$_2$ | 3 |
| 21.2 | 0.7 | CH$_3$ | f |
| 20.9 | 1 | CH$_3$ | 17 |
| 20.6 | 1 | CH$_3$ | 10 |
| 16.6 | 0.7 | CH$_3$ | d |
| 14.7 | 1 | CH$_3$ | 18 |
| 6.7 | 1 | CH$_2$ | 2 |

Figure 2:
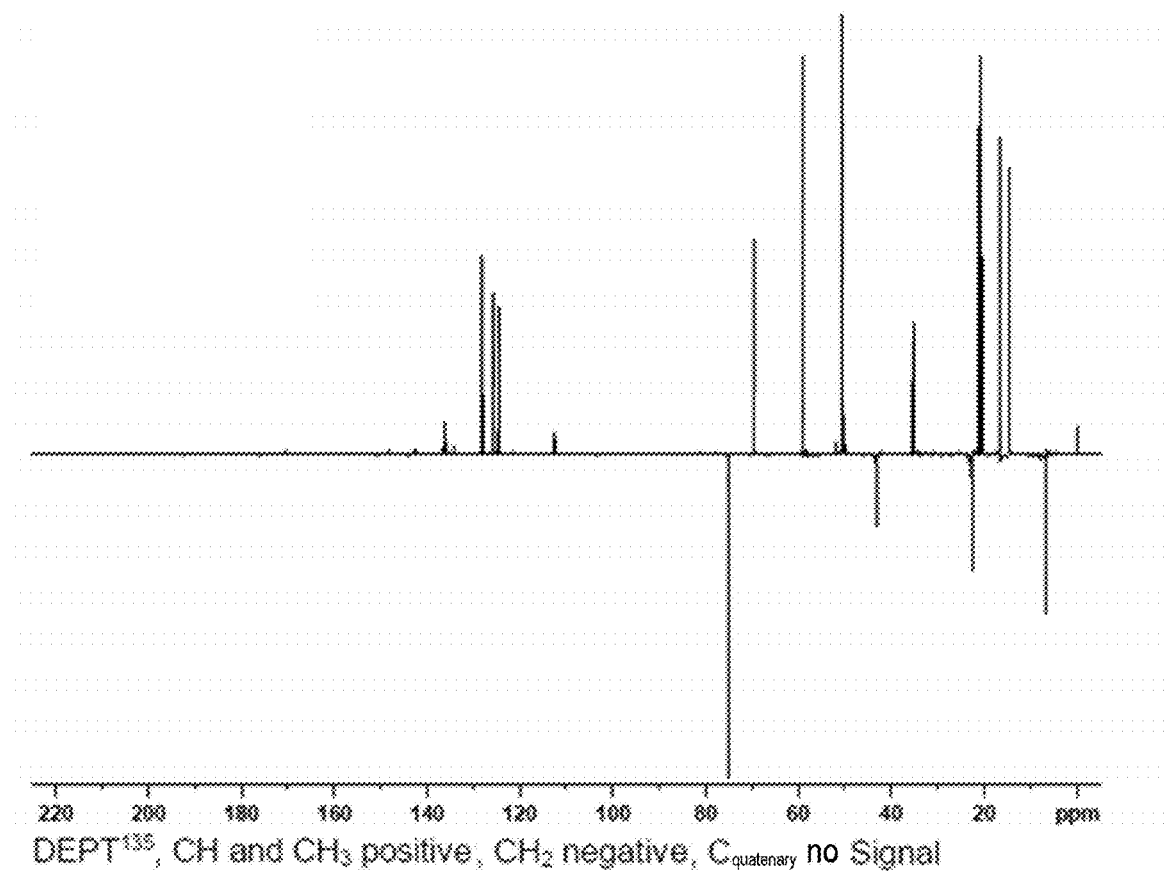

The assignment of the signals of the respective carbon atoms of the compound of the formula (3) according to the invention is characterized in Table 1 by numbers 1-18 and the corresponding assignment of the signals of the solvent residues by letters a-f. The signals having the assignments 6 and 7 in a DEPT experiment of the $^{13}$C-NMR measurement confirm the positions in the heteroaromatic ring as tertiary CH carbons in the compound of the formula (3) according to the invention. FIGS. 1a and 2a which follow give further results of the $^{13}$C-NMR measurements. FIGS. 1b and 2b disclose the respective measurement conditions.

Inventive Example 2: Preparation of the Composition

The adduct prepared from 3-isocyanatopropyltrimethoxysilane and medetomidine from inventive Example 1, the inventive compound of the formula (3), is mixed at room temperature with 3-aminopropyltrimethoxysilane and dibutyl dilauryl stannate in a ratio by weight of 1:0.1:0.001, based on the amount of the adduct of the formula (3) used.

Inventive Example 3: Use of the Composition for Coating Underwater Structures to Protect Against Colonization and/or Growth of Marine Organisms on Underwater Structures The composition obtained in inventive Example 2 is applied as substrate to test plates. The curing is effected at room temperature.

The test plates are mounted on frames and stored in the Hooksmeer/North Sea over a period from May to October. The construction is fixed to buoys and constantly covered with sea water. The respective plates were inspected at regular intervals. From May 2014 a wipe test was carried out by brushing five times in each case from left to right under slight pressure using a hand brush. The final cleaning with high pressure cleaning equipment was carried out at the end of the storage period in October 2014.

Evaluation:

The reaction of 41% by weight medetomidine, 42% 3-isocyanatopropyltrimethoxysilane in 17% propylene glycol monomethyl ether acetate and the paint formulation prepared therefrom based on the commercially available product VESTANAT® EP-MF 201 comprised 12.5% by weight adduct of the compound of the formula (3) according to the invention. The coated plates showed, after the growth phase, growth or biofouling that was easy to remove.

TABLE 2

| Date | Diatom algae | Growth |
| --- | --- | --- |
| 27 May 2014 | Dense colonization | Thick growth of white weed |
| 18 Jun. 2014 | Dense colonization | Thick growth of white weed |
| 11 Jul. 2014 | Dense colonization | Thick growth of white weed |
| 25 Jul. 2014 | Little colonization | Little growth |
| 7 Aug. 2014 | No colonization | Red algae, white weed |
| 22 Aug. 2014 | Few algae | Red algae, white weed |
| 17 Sep. 2014 | Few algae | Fully covered with red algae and white weed |
| 4 Oct. 2014 | Few algae | Fully covered with white weed |
| 20 Oct. 2014 | Few algae | Fully covered with white weed |

The evaluation of the plates shows that an initial growth of diatom algae and white weed occurs but this decreases again or removes itself from the plate after a few weeks. Growth of red algae could be seen after a few weeks but no growth of barnacles was observed over the entire period. The results are summarized in Table 2.

Figure 3:
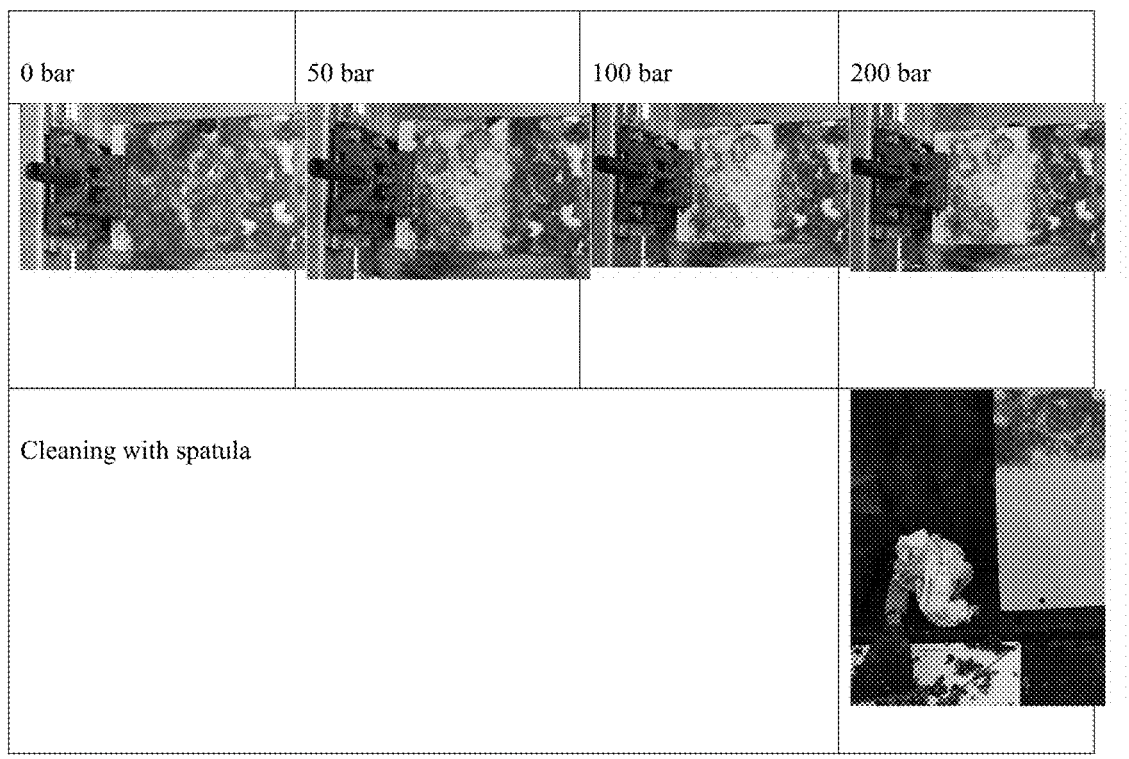
FIG. 3 representatively shows a shows images of cleaning tests with details of the type of cleaning—manually with a spatula or by high pressure cleaning equipment—and the pressure used.

The growth shows only a slight adhesion profile since this may be removed by means of the wipe test. Cleaning with the high pressure cleaning equipment shows almost complete cleaning of the plates and this occurs already at low pressure application. Finally, complete cleaning by light treatment with a spatula could be shown. FIG. 3 which follows shows images in each case of the results of these cleaning tests with details of the type of cleaning—manually with a spatula or by high pressure cleaning equipment—and the pressure used.

Comparative Example: Use of the Composition for Coating Underwater Structures in the Absence of an Adduct of the Compound of the Formula (3) According to the Invention A composition in the absence of medetomidine is prepared and applied as substrate to test plates. The curing is effected at room temperature.

The test plates are mounted on frames and stored in the Hooksmeer/North Sea over a period from May to October. The construction is fixed to buoys and constantly covered with sea water. The respective plates were inspected at regular intervals. From May 2014 a wipe test was carried out by brushing five times in each case from left to right under slight pressure using a hand brush. The final cleaning with high pressure cleaning equipment was carried out at the end of the storage period in October 2014.

Evaluation:

The coated plates in the absence of an adduct of the compound of the formula (3) according to the invention show, after the growth phase, a non-removable growth.

TABLE 3

| Date | Diatom algae | Growth |
| --- | --- | --- |
| 27 May. 2014 | Dense colonization | Little growth |
| 18 Jun. 2014 | Dense colonization | Little growth |
| 11 Jul. 2014 | Dense colonization | Little growth |
| 25 Jul. 2014 | Pronounced colonization | Little growth of isolated white weed |
| 7 Aug. 2014 | Little colonization | Small barnacles |
| 22 Aug. 2014 | Moderate colonization | Organisms greater than 640 |
| 17 Sep. 2014 | Moderate colonization | Small moulds, red algae |
| 4 Oct. 2014 | Moderate colonization | Red algae, barnacles |
| 20 Oct. 2014 | Complete colonization | Barnacles covered with red algae |

The evaluation of the plates shows that an initial growth of diatom algae occurs, this initially increases this but then decreases again or removes itself from the plate after a few weeks. After a few weeks, the growth of white weed and barnacles is observed. The results are summarized in Table 3.

Figure 4:
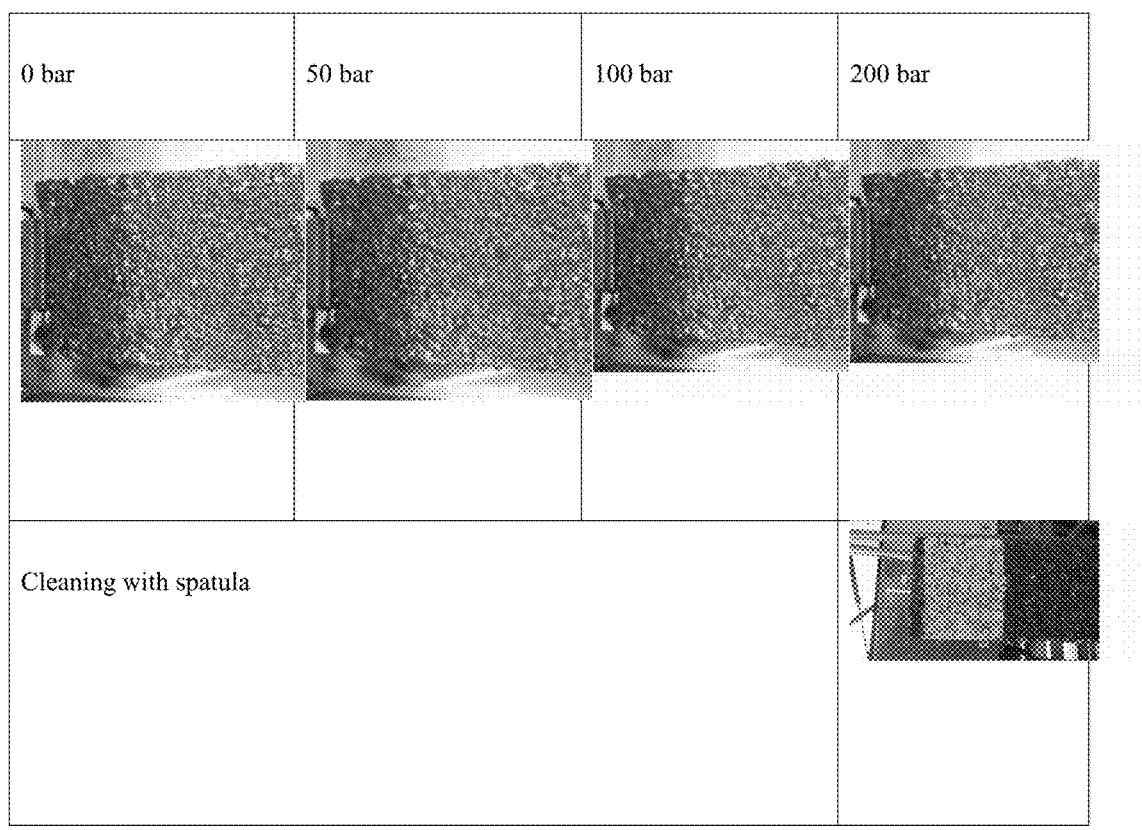
FIG. 4 representatively shows a shows images of cleaning tests with details of the type of cleaning—manually with a spatula or by high pressure cleaning equipment—and the pressure used.

The growth shows a strong adhesion profile such that no cleaning of the plates is achieved by treatment with the high pressure cleaning equipment. Even pressure-resistant treatment with a spatula does not result in complete cleaning. This situation is disclosed in FIG. 4 which follows. It shows images in each case of the results of these cleaning tests with details of the type of cleaning—manually with a spatula or by high pressure cleaning equipment—and the pressure used.

The strong adhesion of the biofouling is particularly clear in that even a high pressure cleaning of up to 200 bar does not result in any visible cleaning success.

The invention claimed is:
1. A compound according to formula (3):
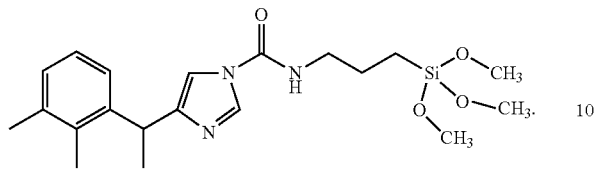
2. A composition, wherein said composition comprises the compound according to claim 1.
3. The composition according to claim 2, wherein said composition comprises an adhesion promoter.